US011318245B2

(12) United States Patent
Henry et al.

(10) Patent No.: US 11,318,245 B2
(45) Date of Patent: May 3, 2022

(54) BODY CAVITY IRRIGATION SYSTEM CONTROLLER

(71) Applicant: Hollister Incorporated, Libertyville, IL (US)

(72) Inventors: Jerome A. Henry, Castlebar (IE); William K. Arnold, Gurnee, IL (US); Donald V. Matesi, Wauconda, IL (US); Denise Gamblin, Leeds (GB); Malford E. Cullum, Grayslake, IL (US)

(73) Assignee: Hollister Incorporated, Libertyville, IL (US)

( * ) Notice: Subject to any disclaimer, the term of this patent is extended or adjusted under 35 U.S.C. 154(b) by 305 days.

(21) Appl. No.: 16/608,960

(22) PCT Filed: Apr. 30, 2018

(86) PCT No.: PCT/US2018/030287
§ 371 (c)(1),
(2) Date: Oct. 28, 2019

(87) PCT Pub. No.: WO2018/201152
PCT Pub. Date: Nov. 1, 2018

(65) Prior Publication Data
US 2020/0179590 A1    Jun. 11, 2020

Related U.S. Application Data

(60) Provisional application No. 62/491,439, filed on Apr. 28, 2017.

(51) Int. Cl.
*A61M 3/02* (2006.01)
*A61M 25/00* (2006.01)

(52) U.S. Cl.
CPC .......... *A61M 3/022* (2014.02); *A61M 3/0258* (2013.01); *A61M 25/0097* (2013.01);
(Continued)

(58) Field of Classification Search
CPC ................ A61M 3/022; A61M 3/0258; A61M 25/0097; A61M 3/0295;
(Continued)

(56) References Cited

U.S. PATENT DOCUMENTS 5,024,212 A * 6/1991 Bonnet .................. A61B 90/05
600/105
2011/0184346 A1    7/2011 Moeller-Jensen et al.
(Continued)

FOREIGN PATENT DOCUMENTS

WO    2012120456 A2    9/2012
WO    2016007536 A1    1/2016
(Continued)

OTHER PUBLICATIONS

International Search Report and Written Opinion of the ISA for PCT Application No. PCT/US2018/030287, dated Sep. 4, 2018 (22 pages).

*Primary Examiner* — Lauren P Farrar
*Assistant Examiner* — Hamza A Darb
(74) *Attorney, Agent, or Firm* — Cook Alex Ltd.

(57) ABSTRACT

A controller for a body cavity irrigation system, where the system features a reservoir containing an irrigation liquid and a catheter, includes a housing with a dial attached to the housing and movable between positions corresponding to stages of a body cavity irrigation procedure. The controller is in communication with an electromechanical pump and at least one electromechanical valve that are in fluid communication with the reservoir and the catheter so that the electromechanical pump and at least one electromechanical valve are configured to perform a stage of the body cavity irrigation procedure corresponding to the selected dial position.

17 Claims, 10 Drawing Sheets

(52) U.S. Cl.
CPC ... *A61M 3/0295* (2013.01); *A61M 2205/3337* (2013.01); *A61M 2205/35* (2013.01); *A61M 2205/586* (2013.01); *A61M 2205/8206* (2013.01); *A61M 2209/01* (2013.01); *A61M 2209/088* (2013.01); *A61M 2210/1067* (2013.01)

(58) Field of Classification Search
CPC ...... A61M 2205/3337; A61M 2205/35; A61M 2205/586; A61M 2205/8206; A61M 2209/01; A61M 2209/088; A61M 2210/1067; A61M 3/0208; A61M 2205/3569; A61M 2205/502; A61M 2210/1092; A61M 2210/1475; A61M 1/76; A61M 1/774; A61M 3/00; A61M 3/02

See application file for complete search history.

(56) References Cited

U.S. PATENT DOCUMENTS

| | | | |
|---|---|---|---|
| 2012/0130347 A1 | 5/2012 | Budig et al. | |
| 2012/0143168 A1 | 6/2012 | Bjerregaard | |
| 2014/0005602 A1* | 1/2014 | Andreen | A61M 3/02 604/98.02 |
| 2017/0252506 A1* | 9/2017 | Frostaa | A61M 3/0208 |
| 2018/0043087 A1* | 2/2018 | Foley | A61M 3/0295 |

FOREIGN PATENT DOCUMENTS

| | | | |
|---|---|---|---|
| WO | 2016041564 A1 | 3/2016 | |
| WO | 2016095928 A1 | 6/2016 | |

* cited by examiner

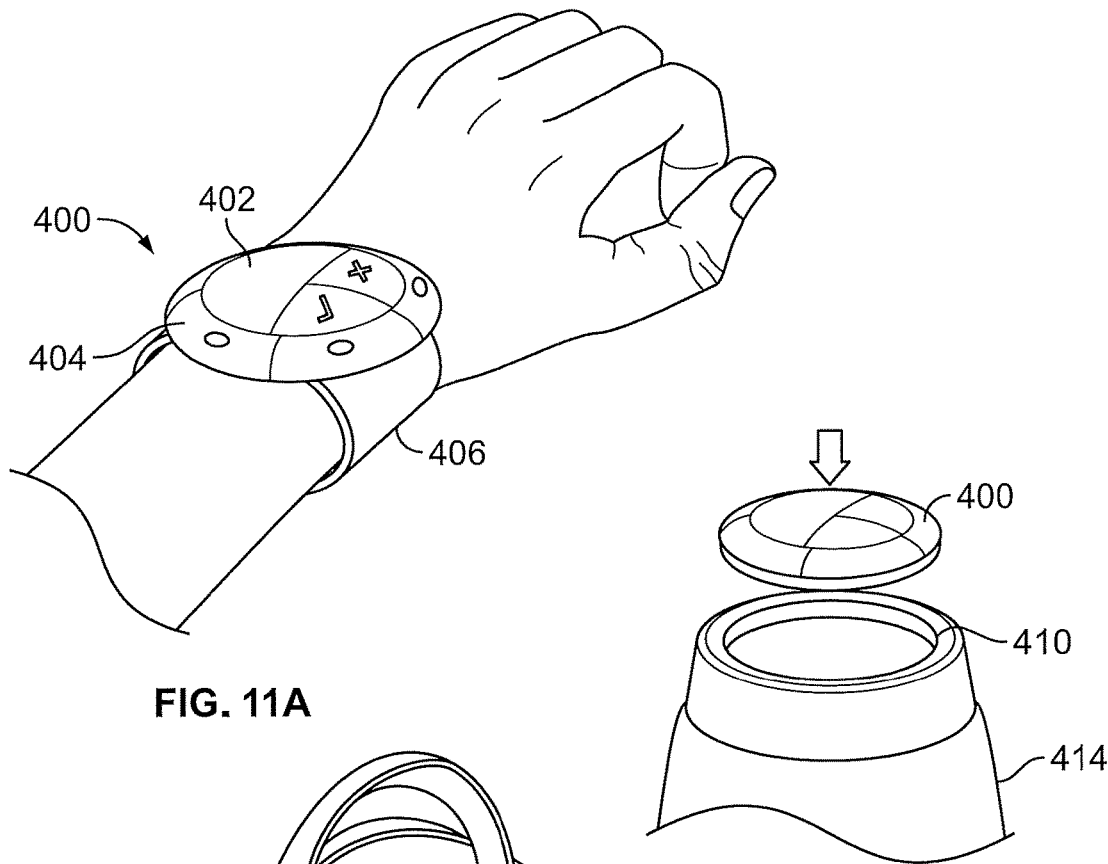
FIG. 11A
FIG. 11B
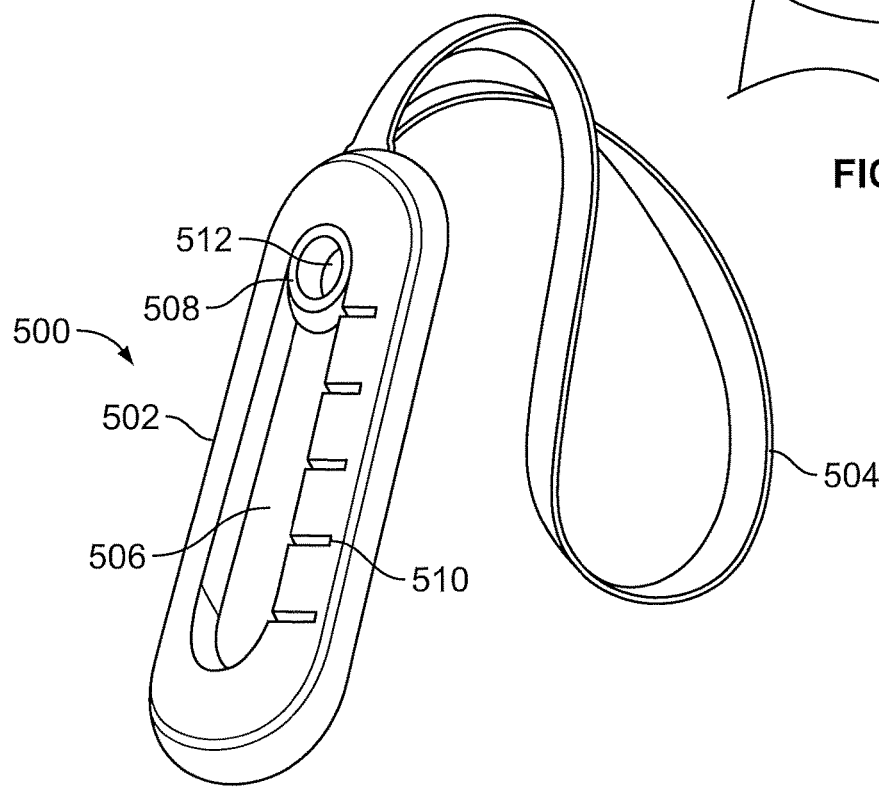
FIG. 12

BODY CAVITY IRRIGATION SYSTEM CONTROLLER

CROSS-REFERENCE TO RELATED APPLICATIONS

The present application is the U.S. National Stage of PCT International Patent Application No. PCT/US2018/030287, filed Apr. 30, 2018, which claims the benefit of and priority to U.S. Provisional Application No. 62/491,439, filed Apr. 28, 2017, the contents of both of which are hereby incorporated herein by reference.

FIELD OF THE INVENTION

The present disclosure relates generally to body cavity irrigation devices, methods and systems and, in particular, to a body cavity irrigation system controller.

BACKGROUND

Transanal irrigation (TAI) is a process used by individuals who have bowel management issues, such as incontinence, constipation or other neurogenic bowel dysfunction (NBD). Alternatively, TAI may be used for regular bowel evacuations by individuals who are incapacitated due to illness or other medical conditions or injuries (such as spinal cord injury) and thus lack the mobility to access a toilet. During TAI, water or other lavage liquid is introduced into the rectum and colon through a device positioned through the anus so that feces are flushed and evacuated. This creates pseudo-continence for the patient/user. Furthermore, individuals that are bedridden may develop fecal impaction. Such bowel obstructions may be removed via TAI.

Systems for performing TAI currently on the market allow the user to introduce water into the bowel through a rectal catheter while the user sits on a toilet or a commode/shower chair or lies in a bed. The user introduces an amount of water or other liquid into the bowel (typically 500-700 mL) in order to flush out stool located in the bowel passage. The user typically introduces the water, waits for a period of time and then allows gravity to flush the water and stool out of the body. The rectal catheter may have an inflatable/deflatable balloon to assist in retention of the catheter during water introduction. The balloon is typically inflated by a fluid such as air or water.

For TAI users, independence, dexterity, and ease of use are important needs that must be addressed by a TAI system or method.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a controller for a body cavity irrigation system, including a reservoir containing an irrigation liquid and a catheter, features a housing with a dial attached to the housing and movable between positions corresponding to stages of a body cavity irrigation procedure. The controller is in communication with an electromechanical pump and at least one electromechanical valve that are in fluid communication with the reservoir and the catheter so that the electromechanical pump and at least one electromechanical valve are configured to perform a stage of the body cavity irrigation procedure corresponding to a selected dial position.

In another aspect, a system for performing a body cavity irrigation procedure includes a reservoir configured to contain an irrigation liquid and a catheter including a curved shaft and a curved hub configured to be gripped by a user. The system also includes a controller that features a housing with a dial attached to the housing and movable between positions corresponding to stages of the body cavity irrigation procedure. The controller is in communication with an electromechanical pump and at least one electromechanical valve that are in fluid communication with the reservoir and the catheter so that the electromechanical pump and at least one electromechanical valve are configured to perform a stage of the body cavity irrigation procedure corresponding to a selected dial position.

BRIEF DESCRIPTION OF THE DRAWINGS

FIG. 11A is a perspective view of a fourth embodiment of the controller of the disclosure;

FIG. 11B is a perspective view of the controller of FIG. 11A being stowed in a base unit;

FIG. 12 is a perspective view of a fifth embodiment of the controller of the disclosure;

DETAILED DESCRIPTION OF EMBODIMENTS

While the embodiments are described below in terms of use in a transanal irrigation (TAI) procedure, it is to be understood that they could instead be used with systems to irrigate other body cavities of a user including, but not limited to, stomas and body cavities accessible by stomas.

Controllers including, or wireless controllers for use with systems including, electromechanical components including pumps and solenoid valves are described below. These variants of controllers can be simply worn on a wrist, or around the user's leg, neck or hand, in accordance with the user's preference. Additionally, some of the controllers can be stored within a socket in the reservoir when not in use.

It should be understood that the term "controller", as used herein, includes devices that control electromechanical valves and pump(s) of a TAI system, whether the electromechanical components are incorporated into the controller itself or in other devices of the system.

Figure 1:
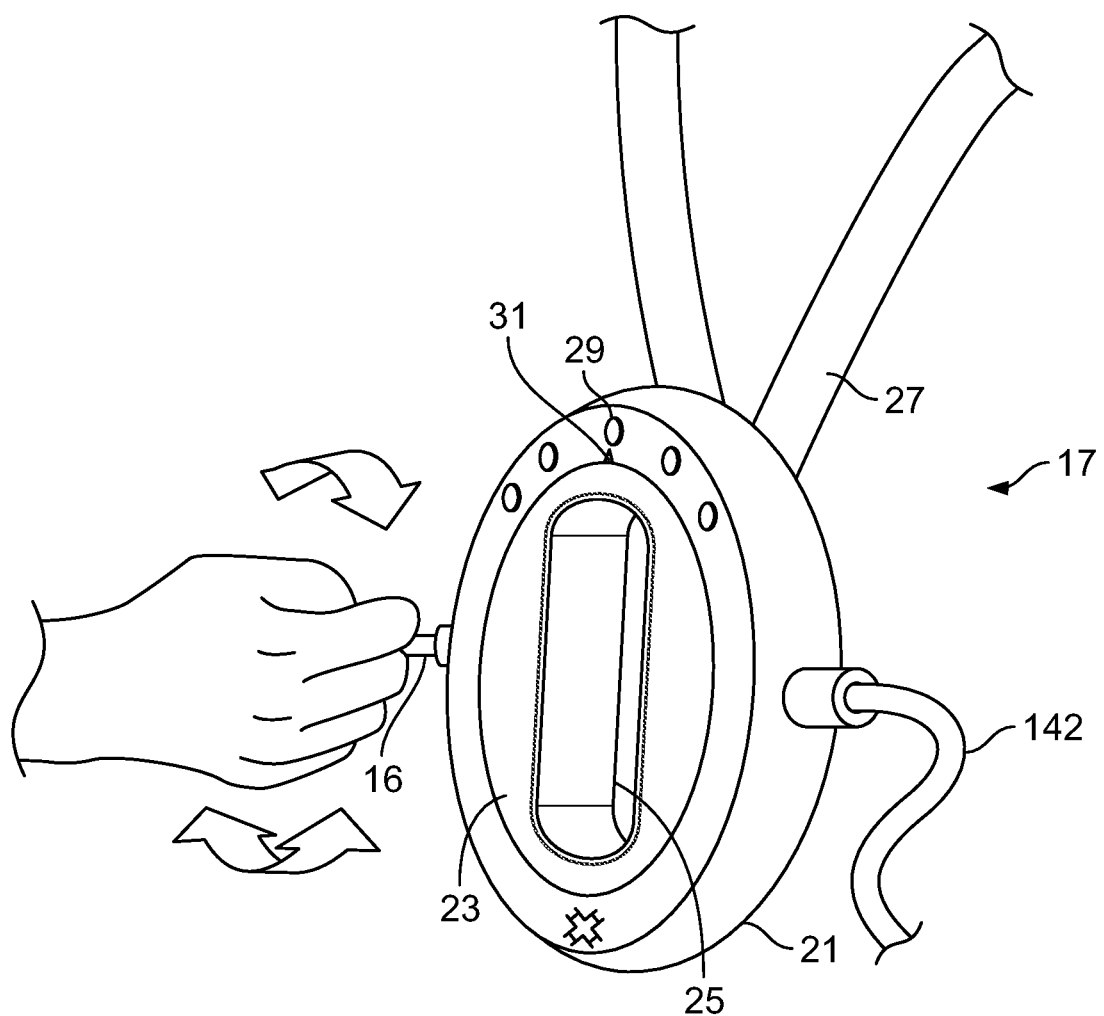
FIG. 1 is a perspective view of a first embodiment of the controller of the disclosure.

In the embodiment of FIG. 1, a controller 17 features a housing 21, which may have a circular shape, with a rotating dial 23 in the center. The dial 23 features an elongated opening 25. The user simply needs to place their hand through the elongated opening 25 to rotate the dial 23 to operate the controller. The controller 17 may be supported, as an example only, by a lanyard 27 worn around the user's neck. Hence, the user does not need to grip this controller in order to operate it. Such an arrangement is advantageous for people with poor dexterity. By rotating their hand or wrist, the user can select through the four different stages of a TAI procedure, i.e. priming, inflating the retention balloon, instilling water, deflating the retention balloon. These four stages are represented by icons or hash marks 29 formed on the housing 21. An arrow 31 formed on the dial 23 aligns with the hash mark corresponding to the selected stage. The fifth hash mark corresponds to a dial position that is selected to turn off the controller. In one example of use, when the controller is worn around the neck, the user may press the controller against his or her chest or abdomen to hold the controller in place while turning the dial.

The controller of FIG. 1 may be used with a trans-anal irrigation (TAI) system. In addition to the controller of FIG. 1, the main components of the system include an irrigation liquid reservoir, fluid tubing, and a rectal catheter. In addition, the system includes electromechanical valves and pump(s) for controlling the flow of irrigation liquid between the reservoir and the catheter. As explained below, these electromechanical components may be located in the controller, in the reservoir or in another device or component within the system.

Figure 2:
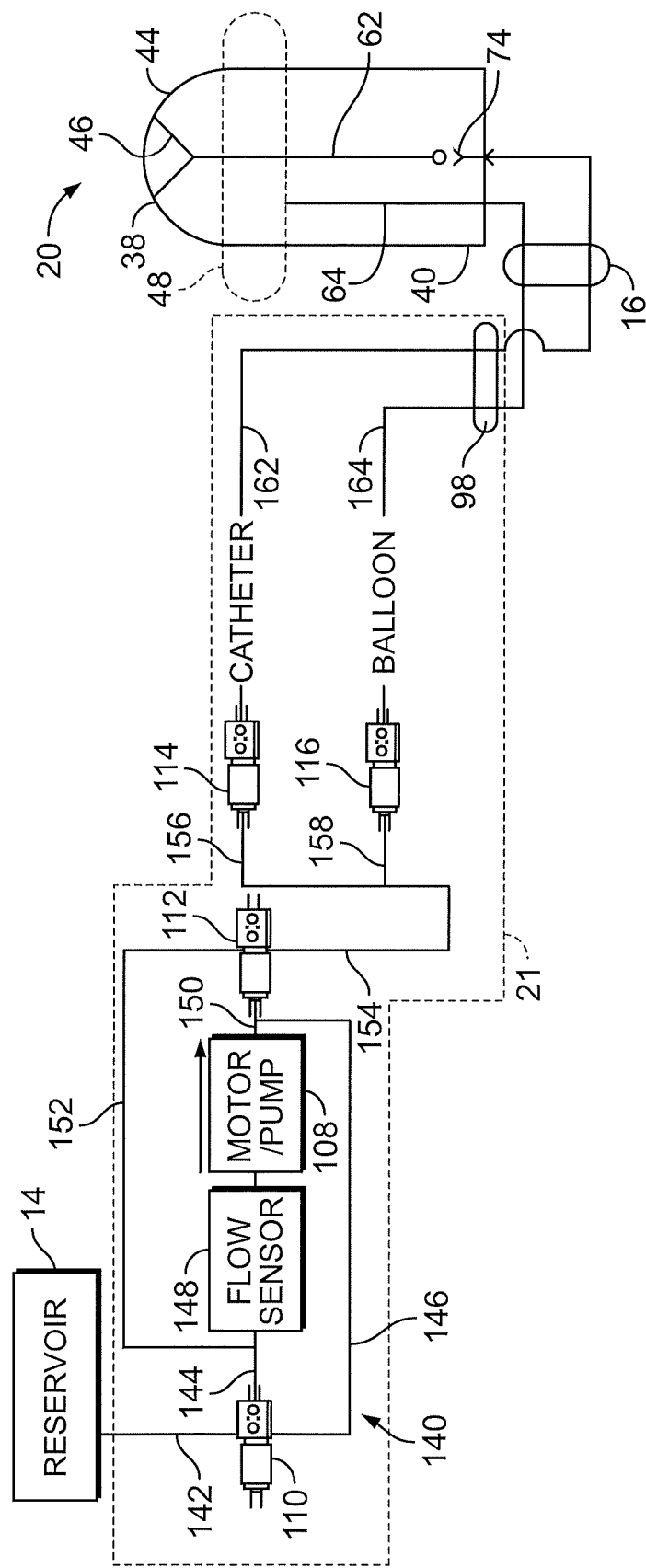
FIG. 2 is a schematic of a hydraulic control circuit in an embodiment of the present disclosure.

FIG. 2 illustrates features of an example of the rectal catheter, indicated in general at 20. The rectal catheter has a hollow shaft which has a patient-proximal end 38 and a patient-distal end 40. The patient proximal end 38 features a rounded tip 44 featuring apertures 46. While two apertures are illustrated in FIG. 2, the catheter may include a different number of apertures. The apertures 46 provide fluid communication with the flushing passage 62 in the interior of the catheter.

A retention balloon 48 (shown in phantom in the inflated state in FIG. 2) is mounted on the exterior of the catheter at a location near the patient-proximal end 38. The retention balloon is in fluid communication with a balloon passage 64 of the catheter. The patient-proximal end of the catheter, including the deflated retention balloon 48, will be inserted into the rectum during a TAI procedure.

As illustrated in FIG. 2, the system includes a pump 108 for pumping water, or another flushing liquid, to the catheter of the system during a TAI procedure. In addition, the system includes solenoid valves 110, 112, 114 and 116 for properly directing the flushing liquid. Embodiments of the controller 17 of FIG. 1 may either incorporate these electromechanical components within the controller housing 21, or, when the controller 17 is a wireless controller, in an alternative location, such as in the flushing liquid reservoir 14.

Figure 3:
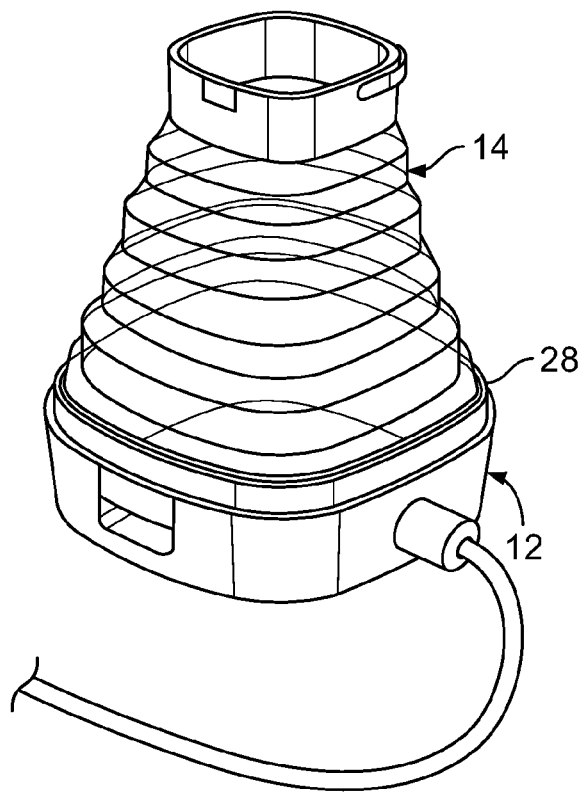
FIG. 3 is a perspective view of an irrigation liquid reservoir suitable for use with some embodiments of the controller of the disclosure.
Figure 4:
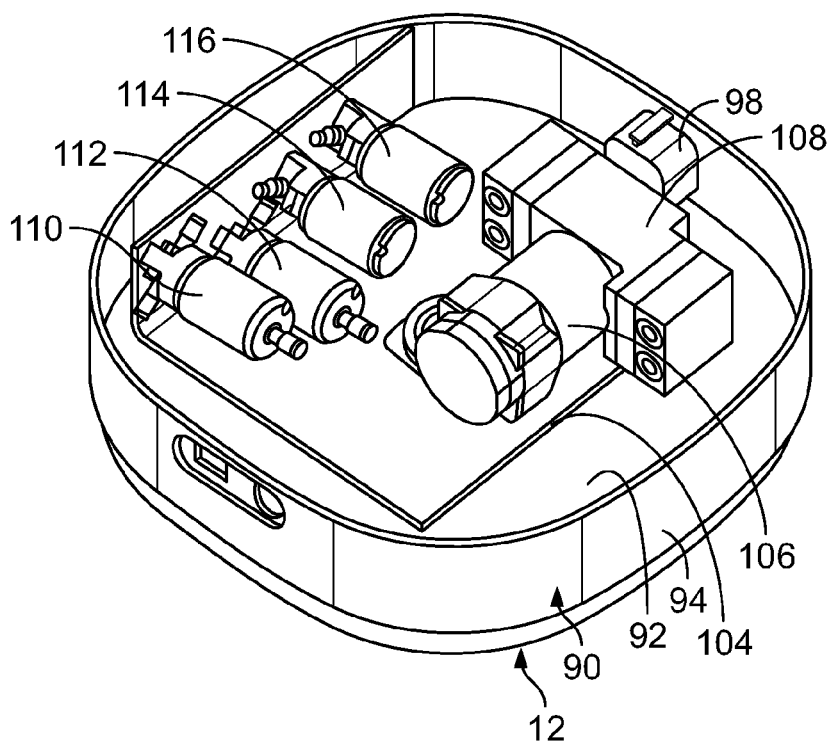
FIG. 4 is a perspective view of the reservoir of FIG. 3 with the liquid tank removed to expose the electromechanical pump/motor and the solenoid valves.

An example of a reservoir 14 suitable for use in embodiments where controller 17 is a wireless controller is presented in FIGS. 3 and 4. The reservoir 14 includes a pump base unit 12 that has, as illustrated in FIG. 4, a generally hollow shell 90 which includes a floor 92 and a perimeter wall 94. The wall 94 supports the base plate 28 (FIG. 3) of the reservoir 14.

Looking at FIG. 4, inside the shell 90 there is a mounting plate 104 which supports an electric motor 106, that operates the pump 108, and the four solenoid valves. While four solenoid valves are illustrated, an alternative number and type of valves may be used. As noted above, the solenoid valves include a reservoir flow director valve 110, a pump flow director valve 112, a catheter valve 114 and a balloon valve 116. Solenoid valves 110 and 112 are normally-open, three-way valves. Solenoid valves 114 and 116 are normally-closed, two-way valves. Not shown but present within the shell 90 are a receiver, a rechargeable battery for powering the pump 108 and internal tubing which provides various fluid connections among the solenoid valves 110-116, the reservoir conduit, the pump 108 and a fitting 98. The fluid connections provided by the internal tubing are described below with reference to the fluid circuit diagrams (FIGS. 2 and 5-8).

FIG. 2 illustrates the hydraulic control circuit 140 in an embodiment of the present disclosure. In addition to the items previously described, the hydraulic control circuit 140 includes a reservoir conduit 142 providing fluid communication between the reservoir 14 and the reservoir flow director valve 110. The reservoir flow director valve 110 is further connected to a pump inlet conduit 144 and a reservoir recirculation conduit 146. Pump inlet conduit 144 joins a flow sensor 148 which in turn is fluidly connected to the motor/pump unit 108. A pump outlet conduit 150 connects the pump 108 to the pump flow director valve 112. The reservoir recirculation conduit 146 branches off of the pump outlet conduit 150. The pump flow director valve 112 is connected to a pump recirculation conduit 152 which in turn joins the pump inlet conduit 144. The pump flow director valve 112 is further connected to a distributor conduit 154. The distributor conduit joins a catheter branch 156 and a balloon branch 158. The branch lines 156 and 158 connect to the catheter valve 114 and the balloon valve 116, respectively.

A fitting 98 connects to the fluid tubing 16. Specifically, the fitting 98 provides fluid communication between: a) catheter supply lumen 162 and flushing passage 62 of the catheter 20; and b) balloon supply lumen 164 and the balloon passage 64 of the catheter 20. While the lumens 162 and 164 are illustrated as being incorporated into a single fluid tubing 16, it is to be understood that the lumens could be incorporated into separate individual tubing.

The use, operation and function of the hydraulic control circuit 140 are as follows, regardless if the electromechanical components are located in the controller 17 (FIG. 1) or the base 12 of the reservoir 14 (FIGS. 3 and 4).

The reservoir 14 is first filled with warm tap water, at the appropriate temperature (between 36° C. and 38° C.). As noted previously, alternative irrigation liquids may be used.

In the following description of the hydraulic control circuit 140, passageways that are closed by one of the solenoid valves 110-116 are shown with an X through them.

In addition, any blocked passageways at a particular stage are shown in dotted lines to indicate that no flow is active in that passageway at the stage under consideration. Arrows indicate the direction of active flow.

Figure 5:
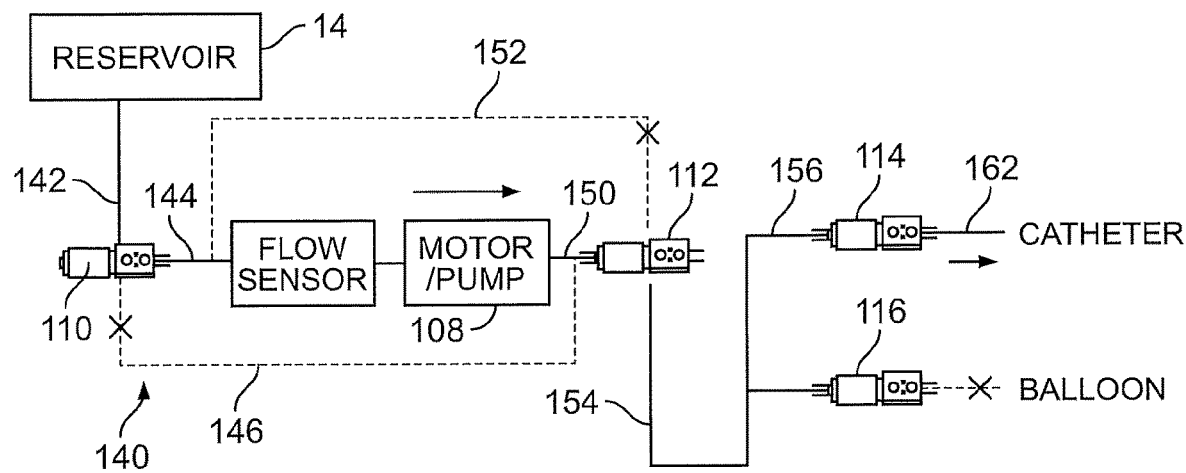
FIG. 5 illustrates the state of the hydraulic control circuit during stage 1, which is the priming of the catheter.

FIG. 5 illustrates stage 1 of the operation. Stage 1 is the priming stage. Before the catheter is inserted into the rectum, the catheter supply lumen 162 of tubing 16 and flushing passage 62 of the catheter 20 need to be primed in order to remove any air therein.

With reference to FIG. 1, the user will select the first icon or hash mark 29 on the controller 17 by rotating the dial 23 to the appropriate position. For this stage, with reference to FIG. 5, the reservoir flow director valve 110 opens the reservoir conduit 142 and the pump inlet conduit 144 and closes the reservoir recirculation conduit 146. The pump flow director valve 112 closes the pump recirculation conduit 152 and opens pump outlet conduit 150 and the distributor conduit 154. The balloon valve 116 remains closed while the catheter valve 114 is opened. This permits flow of irrigation liquid, via the catheter branch 156, to the catheter supply lumen 162 and thus to flushing passage 62 (FIG. 2) of the catheter 20 and out of eyelets or apertures 46.

With the passageways in and to the catheter primed, the catheter will be safely inserted into the rectum in accordance with the clinician's training. Stage 2 can then begin. This is the balloon inflation stage. The user will select the second hash mark 29 on the controller 17 of FIG. 1 by turning the dial 23 to the appropriate position. The volume of water to be pumped into the retention balloon 48 will be pre-defined and will vary from user to user. The controller 17 preferably has a programming mode in which the volume can be set. The volume can also be increased on a manual basis during the TAI procedure if need be, e.g., if leakage occurs after irrigation water is introduced into the rectum.

Figure 6:
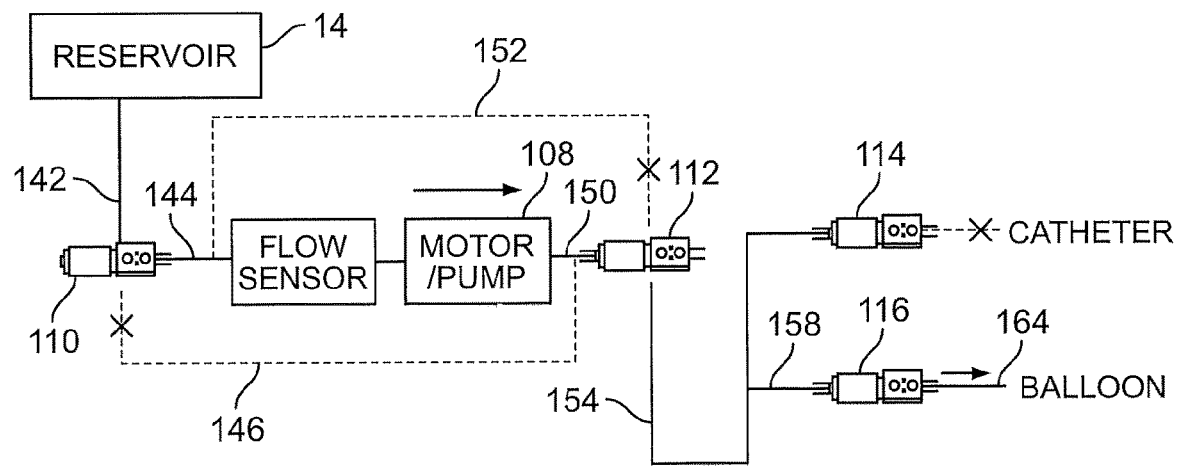
FIG. 6 illustrates the state of the hydraulic control circuit during stage 2, which is inflating the catheter balloon.

During balloon inflation the hydraulic control circuit is set as in FIG. 6. For this stage 2 the reservoir flow director valve 110 opens the pump inlet conduit 144 and closes the reservoir recirculation conduit 146. The pump flow director valve 112 closes the pump recirculation conduit 152 and opens the distributor conduit 154. The catheter valve 114 is closed while the balloon valve 116 is opened. This permits flow to the balloon supply lumen 164 of the fluid tubing 16 via the balloon branch 158. From there water flows to the balloon passage 64 (FIG. 2) of the catheter and ultimately to the interior of the retention balloon 48. This results in the balloon volume increasing, as in FIG. 2, thus retaining the catheter inside the rectum.

With the catheter inserted and the balloon inflated, the next stage can begin. This is stage 3, the introduction of irrigation fluid (most commonly water) into the rectum. During this stage, the flow of liquid may be continuous or it may be a pulsatile flow by turning the pump motor 106 or pump flow director valve 112 on and off rapidly. The user will select the third hash mark on the controller 17 of FIG. 1 by turning the dial 23 to the appropriate position. In one embodiment the user can pre-program a set volume.

Figure 7:
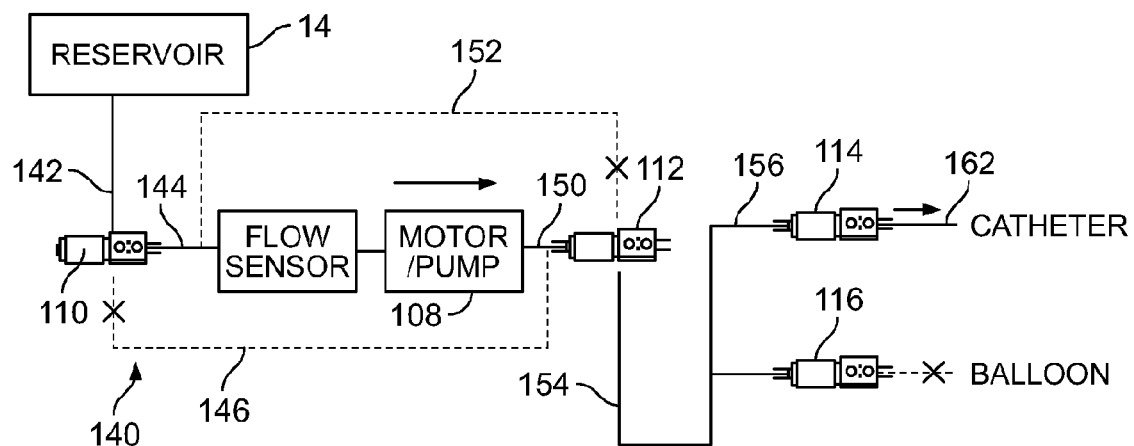
FIG. 7 illustrates the state of the hydraulic control circuit during stage 3, which is providing irrigation liquid to the catheter for flushing.

The condition of the hydraulic control circuit during stage 3 is shown in FIG. 7. The reservoir flow director valve 110 opens the pump inlet conduit 144 and closes the reservoir recirculation conduit 146. The pump flow director valve 112 closes the pump recirculation conduit 152 and opens the distributor conduit 154. The balloon valve 116 is closed while the catheter valve 114 is opened. This permits flow of irrigation liquid to the catheter supply lumen 162 of the fluid tubing 16 via the catheter branch 156. From there, water flows to the flushing passage 62 in the catheter and ultimately out the apertures 46 to the rectum. Once the required amount of irrigant has been pumped, the motor will turn off and the catheter valve 114 is closed.

Note that the check valve 74 (FIG. 2) in the flushing passage 62 of the catheter permits irrigation liquid to flow through the catheter and out of apertures 46, but prevents flow in the opposite direction. This prevents any fecal matter from contaminating the fluid tubing 16.

After the appropriate volume of water has been inserted into the rectum, it shall be allowed to irrigate the rectum for a defined period of time.

When the defined period of time for irrigating the rectum has passed, the catheter needs to be removed from the rectum. To do this, the retention balloon 48 must be deflated. The patient selects the stage 4 hash mark 29 of the controller 17 of FIG. 1 by rotating the dial 23 to the appropriate position.

Figure 8:
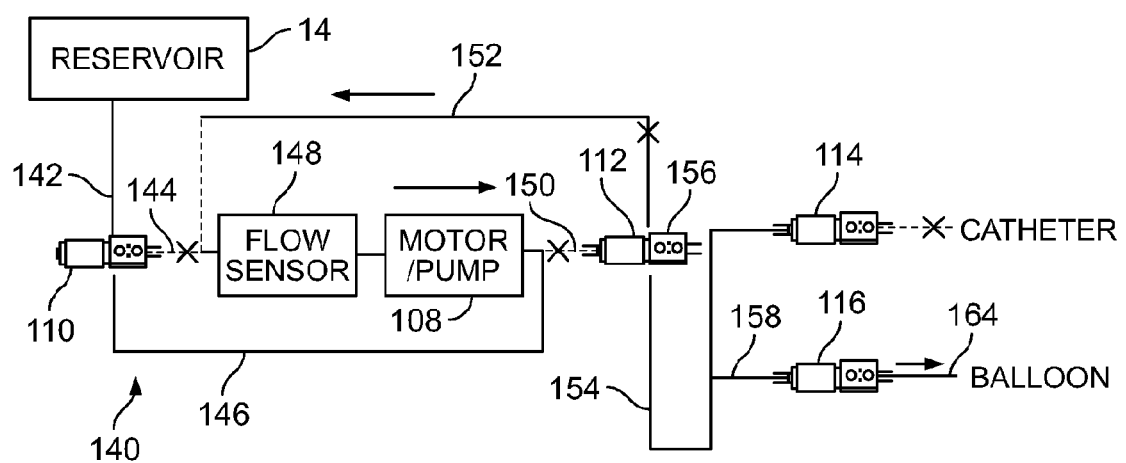
FIG. 8 illustrates the state of the hydraulic control circuit during stage 4, which is deflating the catheter balloon.

The condition of the hydraulic control circuit during stage 4 is shown in FIG. 8. The reservoir flow director valve 110 closes the pump inlet conduit 144 and opens the reservoir recirculation conduit 146. Also, the pump flow director valve 112 opens the pump recirculation conduit 152 and closes pump outlet conduit 150. The distributor conduit 154 remains open. The catheter valve 114 is closed while the balloon valve 116 is opened. The pump is turned on. This permits a reverse flow of liquid from the retention balloon 48 to the balloon valve 116, to the balloon branch 158, to the distributor conduit 154, through the pump flow director valve 112, to the pump recirculation conduit 152, to the flow sensor 148, and to the pump 108. From there the pump directs the water to the reservoir recirculation conduit 146, through the reservoir flow director valve 110 and reservoir conduit 142 and ultimately back to the reservoir 14. As a result, the retention balloon 48 deflates. The pump 108 is turned on long enough to return the same amount of liquid that was put into the retention balloon initially during the inflation stage 2. Once the retention balloon 48 is fully deflated, the pump is turned off and the flow director valves are de-energized. The user can then safely remove the catheter 20 (FIG. 2) from the rectum. The irrigation liquid and fecal matter is then expelled from the rectum.

With reference to FIG. 2, in an alternative embodiment, the controller housing 21 of FIG. 1 (represented in phantom in FIG. 2) may contain the series of electromechanical pump and solenoid valves to control the flow of water or other flushing liquid during a TAI procedure. The electromechanical components are arranged in a circular manner within the controller housing 21, and line 142 of FIG. 2 enters the housing 21, as is illustrated in FIG. 1, while line 16 of FIG. 2 exits the housing 21, as is also illustrated in FIG. 1.

Figure 9:
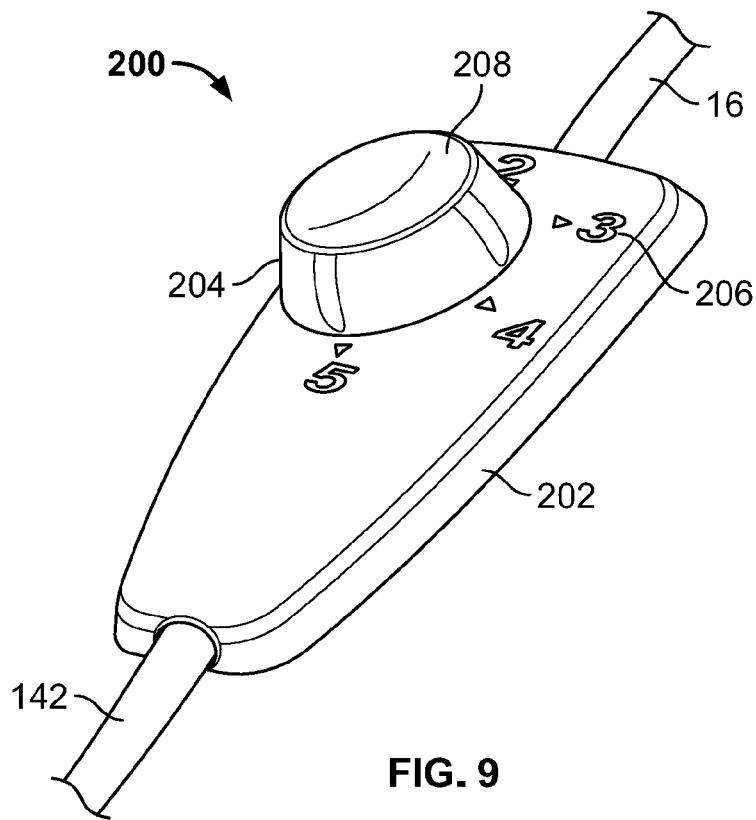
FIG. 9 is a perspective view of a second embodiment of the controller of the disclosure.

A second embodiment of the controller of the disclosure is indicated in general at 200 in FIG. 9. The controller 200 includes a housing 202 upon which a stage selector dial 204 is rotatably mounted. The housing 202 features numerals or other markers 206 indicating stages of a TAI procedure. The dial 204 features an arrow or other marking 208 which may be aligned with the desired stage marking on the housing. The controller housing 202 contains the electromechanical pump and solenoid valves, illustrated in FIGS. 2 and 5-8, to control the flow of water between the TAI system reservoir and catheter. Line 142 of FIG. 2 enters the housing 202, as is illustrated in FIG. 9, while line 16 of FIG. 2 exits the housing 202, as is also illustrated in FIG. 9.

Figure 10A:
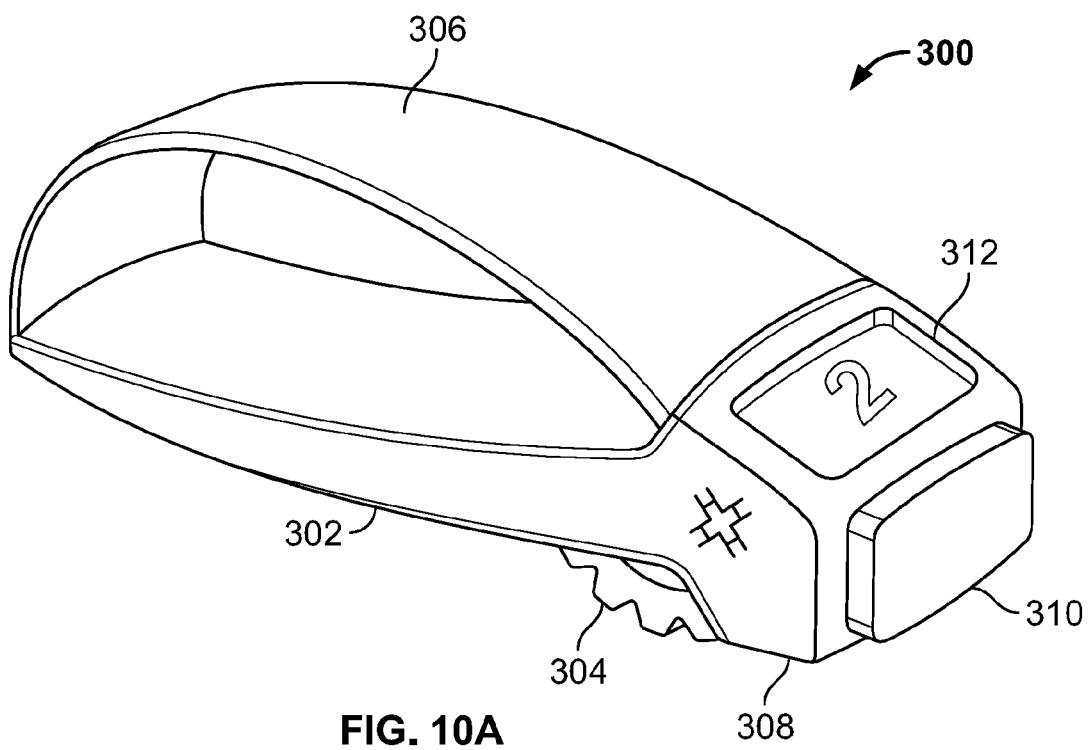
FIG. 10A is a perspective view of a third embodiment of the controller of the disclosure.
Figure 10B:
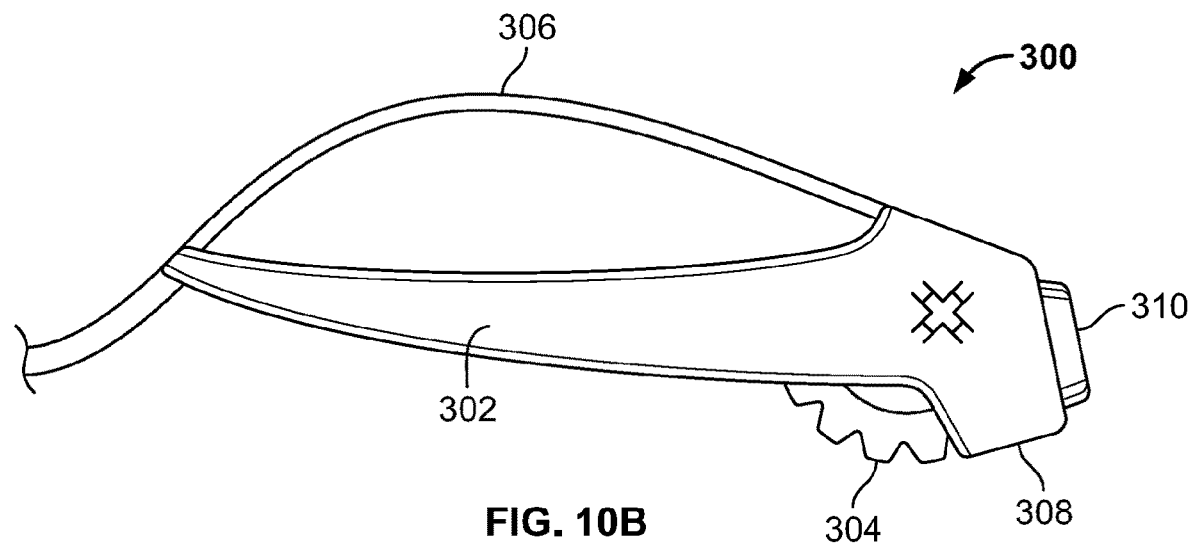
FIG. 10B is a side elevational view of the controller of FIG. 10A.

A third embodiment of the controller of the disclosure, which may provide for both wired and wireless operation of the TAI system, is indicated in general at 300 in FIGS. 10A and 10B. The controller features a housing 302 within which a rotary dial 304 is mounted. The rotary dial 304 is used to transition through the four different stages of a TAI procedure (described above with reference to FIGS. 5-8). When the controller is wireless, it may contain a battery and a transmitter that communicates with a base unit, such as the reservoir 14 of FIGS. 3 and 4, which contains a receiver and the electromechanical pump and solenoid valves to control the flow of water, or other irrigation liquid, between a reservoir (14 in FIG. 2) and a catheter (20 in FIG. 2) via wireless technology such as Bluetooth, RFID, etc.

Figure 10C:
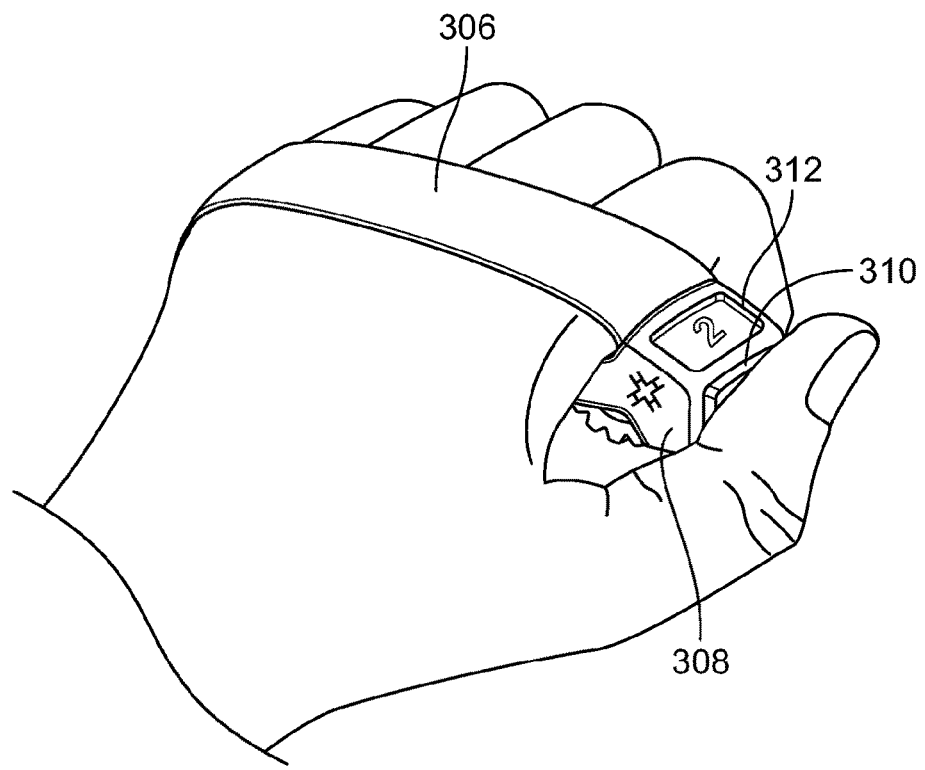
FIG. 10C is a perspective view showing the controller of FIGS. 10A and 10B being held in a hand of a user.

The controller 300 preferably includes a strap 306 that can be adjusted to fit any hand size (as illustrated in FIG. 10C). There is an ergonomically-shaped thumb rest 308 on the side of the housing 302 which has a pushbutton 310 which activates a controller start/pause function. The rotary dial 304 is deliberately on the underside of the housing 302, so that users with no/limited dexterity can use the controller. More specifically, operation of the controller involves moving it in a lateral motion so that the rotary dial 304 contacts the user's leg or other surface. This causes the dial to rotate between the four different stages of a TAI procedure, for example, when they wish to progress between priming and retention balloon inflation. The selected stage appears in a readout window 312, as illustrated in FIG. 10A. After a stage is selected, the user presses the pushbutton 310 to commence the stage. The user can also press the pushbutton 310 again to pause the stage while it is in progress.

A fourth embodiment of the controller of the disclosure, which provides wireless operation of the TAI system, is indicated in general at 400 in FIG. 11A. The controller features a housing 402 with a circular geometry and is provided with a wrist strap 406. Pushbuttons 404 are arranged around the periphery of the housing 402 and enable selection of the four TAI stages (described above with reference to FIGS. 5-8). The controller housing 402 contains a battery and a transmitter that communicates, via wireless technology, such as Bluetooth, RFID, etc., with a base unit that houses the electromechanical componentry, such as the reservoir 14 of FIGS. 3 and 4. In one embodiment, illustrated in FIG. 11B, the base unit may include a reservoir 414 having a circular socket 410 at the top within which the controller 400 is placed when not in use. The base unit may optionally also includes charging circuitry to recharge a battery of the controller.

In a fifth embodiment of the controller of the disclosure, indicated in general at 500 in FIG. 12, a wireless controller features an elongated housing 502 to which a neck lanyard 504 is provided for ease of use. The housing contains a battery and transmitter and features an elongated central opening 506 within which a slide switch 508 is installed. The slide switch 508 is moved along the central opening 506, depending on what stage of the TAI procedure the user wishes to select. The housing features icons or hash marks 510 with which the slide switch 508 can be aligned to select a desired stage of the TAI procedure. The slide switch 508 has a large opening 512 so that a thumb or any of the four fingers can fit inside, thus appealing to all levels of hand dexterity. When the slide switch 508 is positioned at the relevant location, it touches a contact block on the controller internal wall, which then activates, via Bluetooth, RFID or some other wireless technology, the appropriate electromechanical pump and solenoid valve functionality in the base unit (such as reservoir 14 of FIGS. 3 and 4).

Figure 13A:
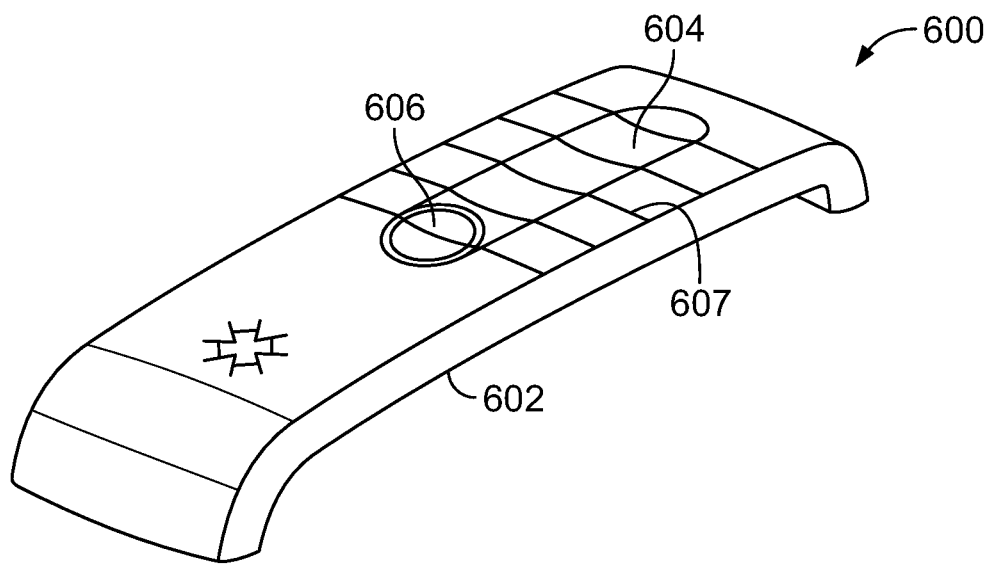
FIG. 13A is a perspective view of a sixth embodiment of the controller of the disclosure.

In a sixth embodiment of the controller of the disclosure, indicated in general at 600 in FIG. 13A, a wireless controller features an elongated housing 602. The housing contains a battery and transmitter and features an elongated recess 604 within which a slide switch 606 is installed. The slide switch 606 can be slid along the recess 604, depending on what stage of the TAI procedure the user wishes to select. The housing features icons or hash marks 607 and corresponding detents with which the slide switch 606 can be aligned and engaged to select a desired stage of the TAI procedure. When the slide switch 606 is positioned at the relevant location, it touches a contact block on the controller internal wall, which then activates, via Bluetooth, RFID or some other wireless technology, the appropriate electromechanical pump and solenoid valve functionality in the base unit (such as reservoir 14 of FIGS. 3 and 4).

Figure 13B:
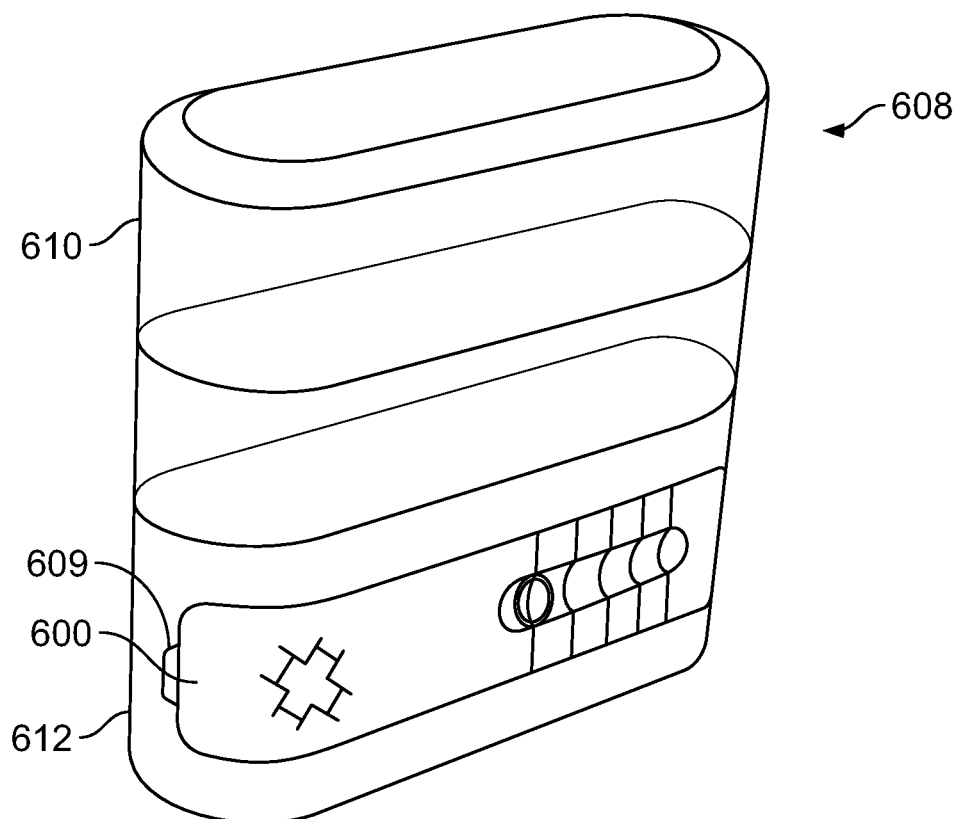
FIG. 13B is a perspective view of the controller of FIG. 13A being stowed in a base unit.

As illustrated in FIG. 13B, a base unit, indicated in general at 608, may feature a socket 609 within which the wireless controller 600 may be placed when not in use. The base unit 608 may include a reservoir tank 610 and a base 612, which houses the electromechanical components of FIG. 4 as well as optional charging circuitry so that the battery of the wireless controller 600 is recharged when the controller is positioned within the socket 609.

Figure 14:
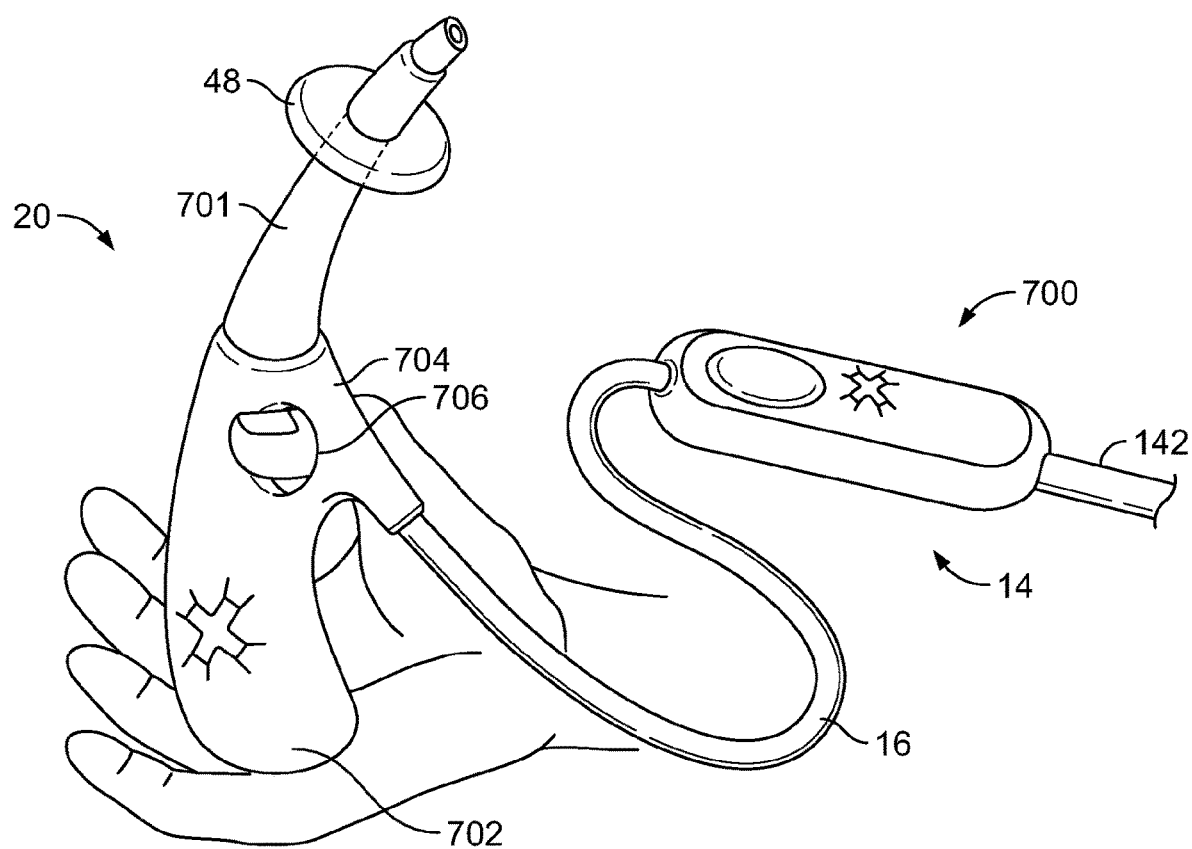
FIG. 14 is a perspective view of a portion of a system in accordance with and embodiment of the disclosure.

A controller of the disclosure is indicated in general at 700 as part of a TAI system in FIG. 14. The TAI system of FIG. 14 includes a catheter 20 having a curved shaft 701 with a curved hub 702 that is shaped to be easily grasped by a user's hand. In addition, the hub preferably incorporates a thumb grip 704 having a thumb opening 706. This overall curved geometry of the catheter 20 is ergonomically designed to make it easier for the user to self-insert a toilet catheter. The thumb grip 704 also enables users having greatly reduced dexterity to self-insert the catheter, i.e. without having to rely on a physician or caregiver to insert it for them.

The controller 700 of the system of FIG. 14 could be either manually operated or electromechanically powered, and could feature the construction of any of the controllers described above.

The controllers described above minimize the amount of physical effort required to transfer water, or any other irrigation liquid, from a reservoir through to a catheter of a TAI system. The controllers also facilitate returning the irrigation liquid from the catheter balloon to the reservoir.

Additionally, some of the controllers have wireless capability, unlike any currently available TAI product. The wireless-controlled inventions are unique as no current TAI device has a similar controller design.

While the preferred embodiments of the disclosure have been shown and described, it will be apparent to those skilled in the art that changes and modifications may be made therein without departing from the spirit of the disclosure, the scope of which is defined by the following claims.

What is claimed is:

1. A controller for a body cavity irrigation system including a reservoir containing an irrigation liquid and a catheter, the controller comprising:
   a housing;
   a dial attached to the housing and rotatably movable relative to the housing between positions corresponding to stages of a body cavity irrigation procedure, the rotatably movable dial including a central opening sized to receive a portion of a user's hand; and
   said controller in communication with an electromechanical pump and at least one electromechanical valve that are in fluid communication with the reservoir and the catheter so that the electromechanical pump and at least one electromechanical valve are configured to perform a stage of the body cavity irrigation procedure corresponding to a selected dial position.

2. The controller of claim 1 wherein the housing contains the electromechanical pump and the at least one electromechanical valve.

3. The controller of claim 1 wherein the housing contains a battery and a transmitter configured to send signals to a base unit that includes the electromechanical pump and the at least one electromechanical valve.

4. The controller of claim 3 wherein the base unit includes the reservoir.

5. The controller of claim 3 wherein the controller is configured to be stored in the base unit.

6. The controller of claim 1 further comprising a lanyard adapted to be worn around a user's neck.

7. The controller of claim 1 further comprising a strap configured to be worn around a hand, arm or leg of a user.

8. A system for performing a body cavity irrigation procedure comprising:
 a reservoir configured to contain an irrigation liquid;
 a catheter including;
 a controller including:
  a housing;
  a dial attached to the housing and rotatably movable relative to the housing between positions corresponding to stages of the body cavity irrigation procedure, the rotatably movable dial including a central opening sized to receive a portion of a user's hand; and
  said controller in communication with an electromechanical pump and at least one electromechanical valve that are in fluid communication with the reservoir and the catheter so that the electromechanical pump and at least one electromechanical valve are configured to perform a stage of the body cavity irrigation procedure corresponding to a selected dial position.

9. The system of claim 8 wherein the housing contains the electromechanical pump and the at least one electromechanical valve.

10. The system of claim 8 wherein the housing contains a battery and a transmitter configured to send signals to a base unit that includes the electromechanical pump and the at least one electromechanical valve.

11. The system of claim 10 wherein the base unit includes the reservoir.

12. The system of claim 10 wherein the controller is configured to be stored in the base unit.

13. The system of claim 8 further comprising a lanyard adapted to be worn around a user's neck.

14. The system of claim 8 further comprising a strap which is configured to be worn around a hand, arm or leg of a user.

15. The system of claim 8, wherein the catheter has a curved shaft.

16. The system of claim 8, wherein the catheter has a curved hub configured to be gripped by a user.

17. The system of claim 16, wherein the curved hub includes an opening for gripping the curved hub.

* * * * *